US010472305B2

(12) United States Patent
Colling et al.

(10) Patent No.: US 10,472,305 B2
(45) Date of Patent: Nov. 12, 2019

(54) HEAT INTEGRATION IN DISPROPORTIONATION OR TRANSALKYLATION PROCESSES

(71) Applicant: BP Corporation North American Inc., Naperville, IL (US)

(72) Inventors: Craig Colling, Warrenville, IL (US); Brian Slusar, Winfield, IL (US)

(73) Assignee: BP Corporation North America Inc., Houston, TX (US)

( * ) Notice: Subject to any disclaimer, the term of this patent is extended or adjusted under 35 U.S.C. 154(b) by 0 days.

(21) Appl. No.: 15/322,335

(22) PCT Filed: Aug. 5, 2015

(86) PCT No.: PCT/US2015/043809
§ 371 (c)(1),
(2) Date: Dec. 27, 2016

(87) PCT Pub. No.: WO2016/022682
PCT Pub. Date: Feb. 11, 2016

(65) Prior Publication Data
US 2017/0152198 A1 Jun. 1, 2017

Related U.S. Application Data

(60) Provisional application No. 62/033,696, filed on Aug. 6, 2014.

(51) Int. Cl.
*C07C 6/06* (2006.01)
*C07C 7/00* (2006.01)
*B01D 3/14* (2006.01)
*C07C 4/14* (2006.01)

(52) U.S. Cl.
CPC ............ *C07C 6/06* (2013.01); *B01D 3/143* (2013.01); *C07C 4/14* (2013.01); *C07C 7/005* (2013.01)

(58) Field of Classification Search
CPC ...................................... C07C 7/005
See application file for complete search history.

(56) References Cited

U.S. PATENT DOCUMENTS

| 4,041,091 A | 8/1977 | Henry | |
| 7,605,295 B1* | 10/2009 | Lafyatis | C07C 6/126 585/475 |
| 2007/0049780 A1* | 3/2007 | Schwartz | C07C 6/126 585/489 |
| 2011/0087000 A1* | 4/2011 | Peters | C07C 2/12 528/308.3 |

(Continued)

FOREIGN PATENT DOCUMENTS

| CN | 101600496 | 12/2009 |
| CN | 103772123 | 10/2012 |

(Continued)

*Primary Examiner* — Philip Y Louie
*Assistant Examiner* — Alyssa L Cepluch
(74) *Attorney, Agent, or Firm* — McDonnell Boehnen Hulbert & Berghoff LLP

(57) ABSTRACT

Toluene disproportionation and C9/C10 transalkylation are a significant source of xylenes in a modern aromatics complex. Methods and apparatuses for improving the energy efficiency of these disproportionation and transalkylation processes are provided.

18 Claims, 4 Drawing Sheets

(56) References Cited

U.S. PATENT DOCUMENTS

2013/0066123 A1\* 3/2013 Lafyatis .................. C07C 6/126
585/312
2013/0261365 A1\* 10/2013 Wang ....................... B01J 37/04
585/475

FOREIGN PATENT DOCUMENTS

| WO | 98/56741 | 12/1998 |
| WO | WO2008/094255 | 1/2007 |

\* cited by examiner though the feedstock for these processes may vary depending on availability and economics, they all have the same goal of maximizing the production of xylene isomers typically through methyl transfer reactions. In some cases these processes also include reactions where molecules like methylethylbenzene are converted to ethane and toluene and this toluene in turn produces even more benzene and xylene isomers. Other common elements of these disproportionation and transalkylation processes include high temperature reaction conditions, consumption and recycle of expensive hydrogen, per-pass conversions significantly below 100%, which leads to large recycles, and energy intensive distillations to recover benzene and C8 aromatics from unconverted feedstocks. There remains a need in the art for improved efficiency in the production of paraxylene by these processes through reducing raw material costs and decreasing the energy consumption.

HEAT INTEGRATION IN DISPROPORTIONATION OR TRANSALKYLATION PROCESSES

CROSS-REFERENCE TO RELATED APPLICATIONS

This application claims benefit of U.S. provisional patent application Ser. No. 62/033,696 filed Aug. 6, 2014, and entitled "Heat Integration in Disproportionation of Transalkyation Process," which is hereby incorporated herein by reference in its entirety.

BACKGROUND

Xylene isomers are produced in large quantities from petroleum and serve as feedstocks for a number of important industrial chemicals. Paraxylene is the principal feedstock for polyester. Orthoxylene is used to produce phthalic anhydride. Metaxylene is used for products such as plasticizers, azo dyes, and wood preservatives. Ethylbenzene generally is present in xylene mixtures and is occasionally recovered for styrene production, but usually is a less desired component of C8 aromatics.

Among the aromatic hydrocarbons, xylenes and benzene are of substantial importance. Neither the xylenes nor benzene are produced from petroleum by the reforming of naphtha in sufficient volume to meet demand, and conversion of other hydrocarbons is necessary to increase the yield of xylenes and benzene. Most commonly, toluene, C9 aromatics, and C10 aromatics are reacted to yield benzene and C8 aromatics from which xylene isomers are recovered. Processes for doing this go by the names of toluene disproportionation, selective toluene disproportionation, and transalkylation. While the feedstock for these processes may vary depending on availability and economics, they all have the same goal of maximizing the production of xylene isomers typically through methyl transfer reactions. In some cases these processes also include reactions where molecules like methylethylbenzene are converted to ethane and toluene and this toluene in turn produces even more benzene and xylene isomers. Other common elements of these disproportionation and transalkylation processes include high temperature reaction conditions, consumption and recycle of expensive hydrogen, per-pass conversions significantly below 100%, which leads to large recycles, and energy intensive distillations to recover benzene and C8 aromatics from unconverted feedstocks. There remains a need in the art for improved efficiency in the production of paraxylene by these processes through reducing raw material costs and decreasing the energy consumption.

Disproportionation and transalkylation processes are generally located near paraxylene production facilities in large process plants called aromatic complexes. In addition to disproportionation, transalkylation, and paraxylene units, aromatics complexes also contain facilities for the purification of primarily benzene and toluene via liquid-liquid extraction or extractive distillation. Paraxylene production facilities are generally comprised of one of two technologies. These two technologies are selective adsorption and crystallization. Selective adsorption facilities for the production of paraxylene are much more energy intensive than crystallization facilities. Consequently, the largest energy consumer in aromatics complexes that employ selective adsorption is the selective adsorption unit and little attention has been paid to the energy efficiency of other units in the aromatics complex like the disproportionation and transalkylation units. With the increased interest for energy efficient crystallization processes for the production of paraxylene, there is a need to increase the energy efficiency of disproportionation and transalkylation units because these units are now becoming the largest consumers of energy in the aromatics complex.

SUMMARY

The present disclosure provides certain advantages and advancements over the prior art. In particular, the present disclosure provides methods and apparatuses for improving the energy efficiency of disproportionation and transalkylation processes.

In one aspect, the disclosure provides processes including the steps of: (a) reacting, in a reactor, a reactor feed stream including toluene, C9 aromatics, C10 aromatics, and hydrogen over a catalyst to produce a reactor effluent stream including benzene and xylenes; (b) cooling the reactor effluent stream to form a first two-phase mixture; (c) separating the first two-phase mixture into a first liquid stream and a first vapor stream; (d) providing at least a portion of the first liquid stream to a benzene column, wherein the portion of the first liquid stream provided to the benzene column bypasses a stabilizer column; and (e) recovering benzene from the first condensed liquid stream in the benzene column. In some embodiments, the processes further include the steps of: (f) cooling the first vapor stream to form a second two-phase mixture; and (g) separating the second two-phase mixture into a second liquid stream and a second vapor stream.

In another aspect, the disclosure provides processes comprising the steps of: (a) reacting, in a reactor, a reactor feed stream comprising toluene, C9 aromatics, C10 aromatics, and hydrogen over a catalyst to produce a reactor effluent stream comprising benzene, toluene, and xylenes; (b) cooling the reactor effluent stream to form a first two-phase mixture; (c) separating the first two-phase mixture into a first liquid stream and a first vapor stream; (d) providing the first liquid stream to a stabilizer column to produce a side draw stream comprising benzene, toluene, and C8 aromatics; and (e) providing the side draw stream to an extractive distillation unit. In some embodiments, the processes further include the steps of: (f) cooling the first vapor stream to form a second two-phase mixture; and (g) separating the second two-phase mixture into a second liquid stream and a second vapor stream.

In another aspect, the disclosure provides apparatuses including: (a) a reactor for reacting a reactor feed stream including toluene, C9 aromatics, C10 aromatics, and hydrogen to produce a reactor effluent stream including benzene, toluene, and C8 aromatics including xylenes; (b) a first cooling apparatus for cooling the reactor effluent stream to produce a first two-phase mixture; and (c) a first separator drum for separating the first two-phase mixture into a first liquid stream and a first vapor stream. In some embodiments, the apparatuses further include: (d) a second cooling apparatus for cooling the first vapor stream to produce a second two-phase mixture; and (e) a second separator drum for separating the second two-phase mixture into a second liquid stream and a second vapor stream. In some embodiments, the apparatuses further include (f) a stabilizer column for receiving the second liquid stream and, optionally, a portion of the first liquid stream; and (g) a benzene column for receiving at least a portion of the first liquid stream, wherein the portion of the first liquid stream provided to the benzene column bypasses the stabilizer column. In other embodiments, the apparatuses further include: (f) a stabilizer column for receiving the first liquid stream and the second liquid stream and for producing a side draw stream including benzene, toluene, and C8 aromatics; and (g) an extractive distillation unit for receiving the side draw stream.

BRIEF DESCRIPTION OF THE DRAWINGS

The following detailed description of the embodiments of the present disclosure can be best understood when read in conjunction with the following drawings in which.

Figure 1:
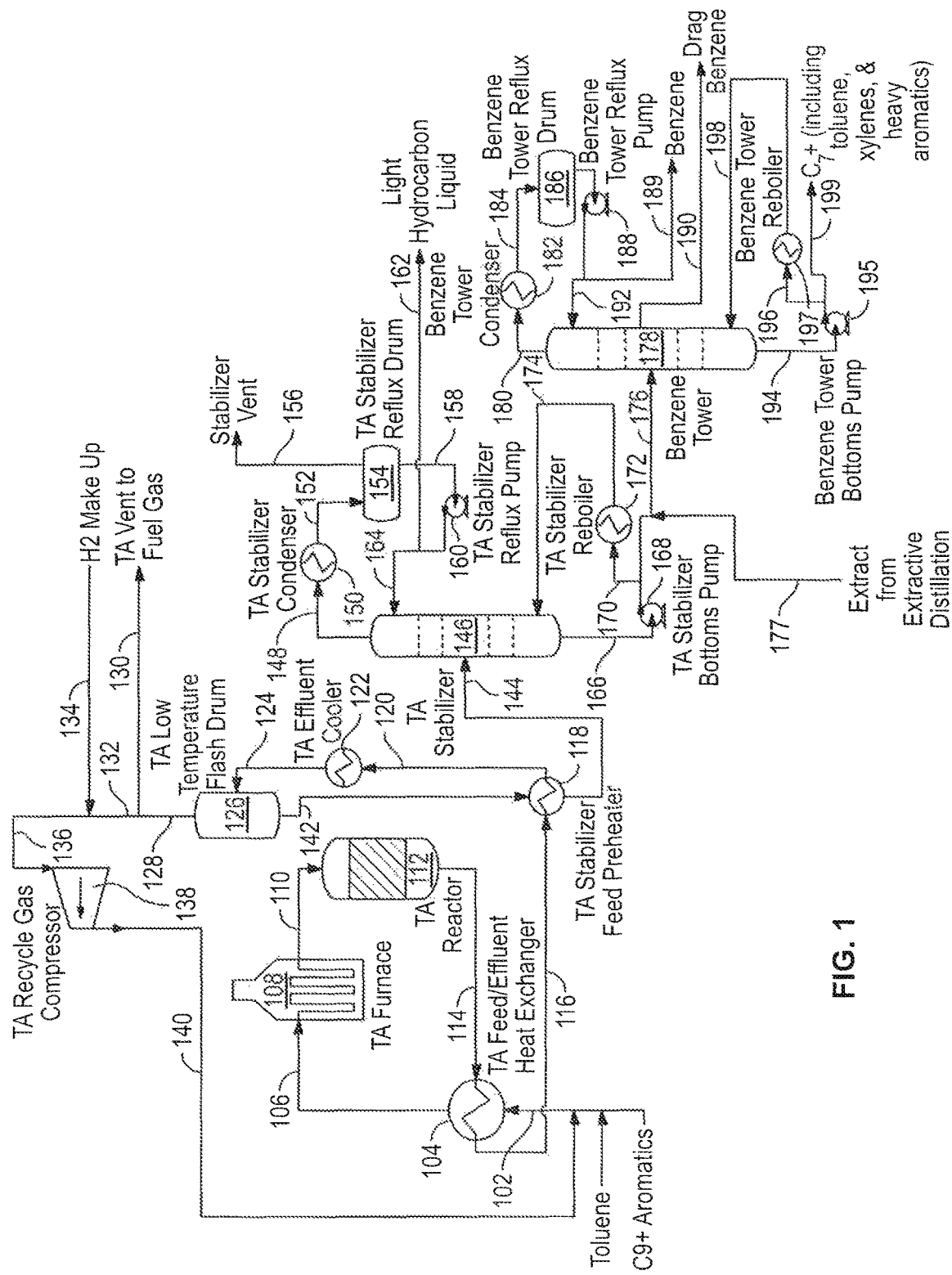
FIG. 1 is a schematic representation of a transalkylation process with benzene recovery, wherein all of the liquid stream exiting a low-temperature flash drum is sent to a stabilizer column.

Skilled artisans will appreciate that elements in the figures are illustrated for simplicity and clarity and have not necessarily been drawn to scale. For example, the dimensions of some of the elements in the figures can be exaggerated relative to other elements to help improve understanding of the embodiment(s) of the present disclosure.

DETAILED DESCRIPTION

All publications, patents and patent applications cited herein are hereby expressly incorporated by reference for all purposes.

Before describing the methods and apparatuses of the present disclosure in detail, a number of terms will be defined. As used herein, the singular forms "a", "an", and "the" include plural referents unless the context clearly dictates otherwise. For example, reference to a "nucleic acid" means one or more nucleic acids.

It is noted that terms like "preferably", "commonly", and "typically" are not utilized herein to limit the scope of the claimed methods and apparatuses or to imply that certain features are critical, essential, or even important to the structure or function of the claimed methods and apparatuses. Rather, these terms are merely intended to highlight alternative or additional features that can or cannot be utilized in a particular embodiment of the present methods and apparatuses.

For the purposes of describing and defining the present methods and apparatuses it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

Xylenes are very valuable feedstocks for many widely used petrochemicals and plastics. Various commercial processes have therefore been developed which convert toluene and C9 alkylaromatics into xylene. These processes involve molecular rearrangements such as the transfer of the methyl groups of toluene to form benzene and xylenes or the transfer of the methyl groups of toluene and trimethylbenzenes to produce xylenes. Other C9 aromatics may undergo other types of reactions. For example, ethyl groups may be transalkylated or dealkylated. These processes are sometimes referred to as disproportionation or transalkylation processes.

As used herein, the terms "disproportionation" or "toluene disproportionation" are interchangeable and refer to a chemical process including the conversion of two toluene molecules into one benzene and one xylene molecule, as shown below:

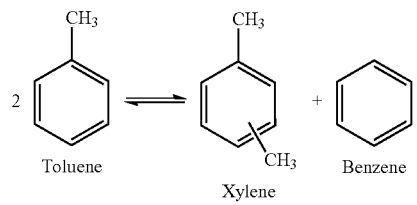

The xylene product may be any xylene isomer, including orthoxylene, paraxylene, and metaxylene.

As used herein, the term "transalkylation" refers to a series of chemical reactions including the transfer or one or more alkyl moieties from one molecule to another. For example, "toluene transalkylation" includes the conversion of a toluene molecule and a C9 aromatic molecule into two xylene molecules, as shown below:

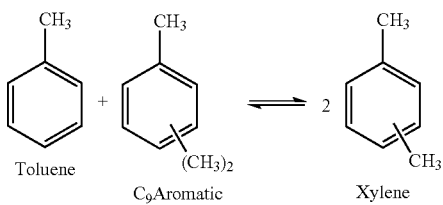

Other transalkylation reactions can involve C9 aromatics (or higher aromatics) and can include a reaction with benzene to produce toluene and xylene, such as:

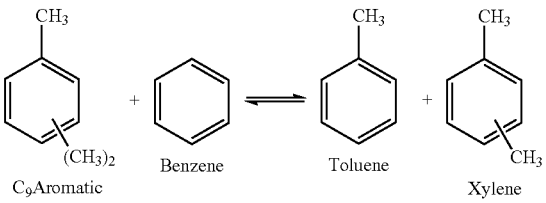

The xylene products and reactants in transalkylation reactions may be any xylene isomer, including orthoxylene, paraxylene, and metaxylene.

Toluene disproportionation and C9/C10 transalkylation are a significant source of xylenes in a modern aromatics complex. Typically, toluene, C9 aromatics, and C10 aromatics are mixed, combined with $H_2$-rich recycle gas and sent to a reactor vessel containing a catalyst, producing a mixture containing desirable benzene and xylenes in addition to unreacted feedstock and light hydrocarbon gases. Catalysts are readily available and typically operate at elevated temperature and pressure. A significant cost in this process is the energy required to heat the reactants to reaction temperature and separate the reactants from the products. It is desired to develop improved processes with enhanced energy efficiency. This disclosure includes several embodiments that improve the energy efficiency of this process.

In general, the economic viability of any process for the production of xylenes is dependent on several factors. One of the most important of these is the yield and overall recovery of the valuable aromatics including benzene and xylenes. Loss of these aromatics to fuel gas and excessive recycle places a heavy economic burden on a process. Another important economic factor in the success of a commercial process is the initial capital cost of the equipment such as columns, reactors and piping and the catalyst necessary for operating the process. Finally, a successful process should be energy efficient. This is measured by the overall operating cost of the process which includes such utility items as heating and cooling streams associated with reactors and fractionation columns and the energy expended in compressing or pumping various fluid streams.

In one embodiment of the methods and apparatuses disclosed herein, feed-effluent heat exchange, in which hot reactor effluent is contacted in a heat exchanger with cool reactor feed, is used to improve energy efficiency. A close approach temperature is desirable to maximize energy efficiency. For example, in some embodiments, the reactor feed is heated to within 50° F. (10° C.) of the reactor effluent temperature. As the reactor effluent is cooled, heavy hydrocarbons (primarily benzene, toluene, xylenes, and C9+ aromatics) begin to condense, forming a two-phase mixture. The two phases can be separated and directed to different parts of the process.

In another embodiment of the methods and apparatuses disclosed herein, the condensation is performed in at least two steps, where the final step occurs near ambient temperature and previous step(s) occur between ambient temperature and reactor temperature. Then, the liquid and vapor formed in each step is separated and the liquid and vapor products are directed to different parts of the process.

For example, it can be desirable to use a feed-effluent heat exchanger to cool the reactor effluent and form a two-phase mixture that can be separated in a high temperature separator. The vapor from the high temperature separator can be cooled by several media, including the reactor feed, to produce two-phase mixtures. The liquid from the high temperature separator is typically free from light hydrocarbons and can be processed directly (e.g. in the benzene column) and can bypass the stabilizer column. The stabilizer column removes dissolved light hydrocarbons from the liquid formed in the final, ambient-temperature, low-temperature separator. This leads to significant fractionation energy savings because material from the high temperature separator bypasses the stabilizer.

Another embodiment of the methods and apparatuses disclosed herein involves heating the low temperature separator liquid with hot vapor from the high temperature separator. This reduces the energy required in the stabilizer.

Specific disproportionation and transalkylation conditions used in conjunction with the methods and apparatuses disclosed herein are, in part, dependent upon the catalyst used for the reaction and its activity as well as the composition of the disproportionation or transalkylation feed. In general, the disproportionation or transalkylation conditions include elevated temperatures, e.g., from about 100° C. to about 425° C., or from about 200° C. to about 400° C. In commercial facilities, the disproportionation or transalkylation temperature is often increased to compensate for any decreasing activity of the catalyst. The feed to a disproportionation or transalkylation reactor may first be heated. The feed then is passed through a reaction zone, which may include one or more individual reactors containing catalyst. The catalyst is typically a silica-alumina or zeolite like dealuminated mordenite, ulta-stable Y-zeolite, ZSM-12, or zeolite beta. Commercially available catalysts include ATA-12 and ATA-21 offered by Zeolyst International and SK Innovation, TA-20 and PXP-300 offered by UOP, and TransPlus offered by Axens.

Transalkylation or disproportionation conditions include pressures ranging from about 100 kPa to about 10 MPa (absolute), or from about 0.5 MPa to about 5 MPa (absolute). The reactions can be effected over a wide range of space velocities. The weight hourly space velocity (WHSV) generally is in the range of from about 0.1 $hr^{-1}$ to about 30 $hr^{-1}$ or from about 0.5 $hr^{-1}$ to about 20 $hr^{-1}$, or between about 1 $hr^{-1}$ to about 5 $hr^{-1}$. For example, transalkylation catalyst reactor conditions might be as follows:

Temperature=400° C.
Pressure=1.4 MPa
H2:HC (hydrogen-to-hydrocarbon ratio):=4:1
WHSV=1.0
Feed Composition:

| Component | Concentration, wt % |
| --- | --- |
| Light Gas | 0.19 |
| Benzene | 0.18 |
| Toluene | 37.51 |
| Ethylbenzene | 0.04 |
| p-Xylene | 0.11 |
| m-Xylene | 0.28 |
| o-Xylene | 0.19 |
| Propylbenzene | 3.99 |
| Methylethylbenzene | 30.75 |
| Trimethylbenzene | 26.08 |
| $A_{10}+$ | 0.54 |

As used herein, the term "extractive distillation unit" refers to a unit, such as a one or more distillation columns, that is capable of extractive distillation. As used herein, the term "extractive distillation" refers to distillation of, for example, a two-component mixture in the presence of a miscible, high-boiling, relatively non-volatile component, called the solvent or separation solvent. The solvent is chosen such that it does not form an azeotrope with the other components in the mixture. The solvent interacts differently with the components of the mixture thereby causing their relative volatilities to change. This enables the new three-part mixture to be separated by normal distillation. The component with the greatest volatility when it enters the extractive distillation unit separates out as the top product. The bottom product consists of a mixture of the solvent and an aromatic component, which can again be separated easily because the solvent does not form an azeotrope with it. The bottom product can be separated in a solvent recovery column into the solvent and the aromatics component.

Extractive distillation is used for mixtures having a low value of relative volatility, nearing unity. Such mixtures cannot be separated by simple distillation, because the volatility of the two components in the mixture is nearly the same, causing them to evaporate at nearly the same temperature at a similar rate, making normal distillation impractical.

It is important to select a suitable separation solvent for extractive distillation. The solvent must alter the relative volatility by a wide enough margin for a successful result.

The quantity, cost and availability of the solvent should be considered. The solvent should be easily separable from the bottom product, and should not react chemically with the components or the mixture, or cause corrosion in the equipment. One example of extractive distillation is the separation of an azeotropic mixture of benzene and cyclohexane, where aniline, sulfolane, N-Formyl morpholine (NFM), and N-Methyl-2-pyrrolidone (NMP) are suitable solvents. In the methods and apparatuses disclosed here, extractive distillation may be used to separate benzene and cyclohexane, methylcyclopentane, and/or C7 isoparaffins in cases where benzene cannot be produced directly by (non-extractive) distillation.

In one aspect, the disclosure provides processes including the steps of: (a) reacting, in a reactor, a reactor feed stream including toluene, C9 aromatics, C10 aromatics, and hydrogen over a catalyst to produce a reactor effluent stream including benzene and xylenes; (b) cooling the reactor effluent stream to form a first two-phase mixture; (c) separating the first two-phase mixture into a first liquid stream and a first vapor stream; (d) providing at least a portion of the first liquid stream to a benzene column, wherein the portion of the first liquid stream provided to the benzene column bypasses a stabilizer column; and (e) recovering benzene from the first condensed liquid stream in the benzene column.

In another aspect, the disclosure provides processes including the steps of: (a) reacting, in a reactor, a reactor feed stream including toluene, C9 aromatics, C10 aromatics, and hydrogen over a catalyst to produce a reactor effluent stream including benzene, toluene, and xylenes; (b) cooling the reactor effluent stream to form a first two-phase mixture; (c) separating the first two-phase mixture into a first liquid stream and a first vapor stream; (d) providing the first liquid stream to a stabilizer column to produce a side draw stream including benzene, toluene, and C8 aromatics; and (e) providing the side draw stream to an extractive distillation unit.

In some embodiments, the processes further include the steps of: (f) cooling the first vapor stream to form a second two-phase mixture; and (g) separating the second two-phase mixture into a second liquid stream and a second vapor stream. In some embodiments, the processes further include providing the second liquid stream to the stabilizer column.

In some embodiments, the first liquid stream is substantially free of light hydrocarbons. In some embodiments, the first liquid stream includes only about 15%, or about 10%, or about 9%, or about 8%, or about 7%, or about 6%, or about 5%, or about 4%, or about 3%, or about 2%, or about 1%, or less than 1% light hydrocarbons.

In some embodiments, the processes further include using the reactor effluent stream to heat the reactor feed stream. In some embodiments, the reactor feed stream is heated to within about 100, or about 90, or about 80, or about 70, or about 60, or about 50, or about 40, or about 30, or about 20 degrees Celsius of the reactor effluent stream. In some embodiments, the reactor feed stream is heated to within about 50 degrees Celsius of the reactor effluent stream.

In some embodiments, the processes further include using the first vapor stream to heat the reactor feed stream. In some embodiments, the reactor feed stream is heated to within about 100, or about 90, or about 80, or about 70, or about 60, or about 50, or about 40, or about 30, or about 20, or about 10 degrees Celsius of the first vapor stream.

In some embodiments, the step of cooling the reactor effluent stream to form the first two-phase mixture is performed at between about ambient temperature and the reactor temperature. In some embodiments, the step of cooling the first vapor stream to form the second two-phase mixture is performed at about ambient temperature. In some embodiments, the processes further include using the first vapor stream to heat the second condensed liquid stream. In some embodiments, the second condensed liquid stream is heated to within about 100, or about 90, or about 80, or about 70, or about 60, or about 50, or about 40, or about 30, or about 20, or about 10 degrees Celsius of the first vapor stream.

In some embodiments of the processes disclosed herein, the processes further include the steps of: (f) cooling the first vapor stream to form a second two-phase mixture; and (g) separating the second two-phase mixture into a second liquid stream and a second vapor stream. In some embodiments, the processes further include providing the second liquid stream to the stabilizer column. In some embodiments, the first liquid stream is substantially free of light hydrocarbons. In some embodiments, the first liquid stream includes only about 15%, or about 10%, or about 9%, or about 8%, or about 7%, or about 6%, or about 5%, or about 4%, or about 3%, or about 2%, or about 1%, or less than 1% light hydrocarbons.

In another aspect, the disclosure provides apparatuses including: (a) a reactor for reacting a reactor feed stream including toluene, C9 aromatics, C10 aromatics, and hydrogen to produce a reactor effluent stream including benzene, toluene, and C8 aromatics including xylenes; (b) a first cooling apparatus for cooling the reactor effluent stream to produce a first two-phase mixture; and (c) a first separator drum for separating the first two-phase mixture into a first liquid stream and a first vapor stream.

In some embodiments, the apparatuses further include: (d) a second cooling apparatus for cooling the first vapor stream to produce a second two-phase mixture; and (e) a second separator drum for separating the second two-phase mixture into a second liquid stream and a second vapor stream. In some embodiments, the apparatuses further include: (f) a stabilizer column for receiving the second liquid stream and, optionally, a portion of the first liquid stream; and (g) a benzene column for receiving at least a portion of the first liquid stream, wherein the portion of the first liquid stream provided to the benzene column bypasses the stabilizer column. In other embodiments, the apparatuses further include: (f) a stabilizer column for receiving the first liquid stream and the second liquid stream and for producing a side draw stream including benzene, toluene, and C8 aromatics; and (g) an extractive distillation unit for receiving the side draw stream.

In some embodiments, the first cooling apparatus uses the reactor feed stream to cool the reactor effluent stream. In some embodiments, the temperature of the first two-phase mixture is between about ambient temperature and the reactor temperature.

In some embodiments, the reactor temperature is between about 380 and 420 degrees Celsius. In certain embodiments, the reactor temperature is between about 390 and 410 degrees Celsius (or from about 734 to about 770 degrees Fahrenheit).

In some embodiments, the temperature of the first two-phase mixture is from about 25% to about 40% of the reactor temperature, or from about 28% to about 35% of the reactor temperature. In some embodiments, the temperature of the first two-phase mixture is from about 115 to about 130 degrees Celsius, or from about 121 to 127 degrees Celsius (about 250 to about 260 degrees Fahrenheit).

In some embodiments, the second cooling apparatus uses the reactor feed stream to cool the first vapor stream in the second cooling apparatus, thereby producing the second two-phase mixture. In some embodiments, the temperature of the second two-phase mixture is about ambient temperature. In some embodiments, the temperature of the second two-phase mixture is about 100% to about 200% of ambient temperature, or about 120% to about 150% of ambient temperature. In some embodiments, the temperature of the second two-phase mixture is about 30 to about 50 degrees Celsius, or about 35 to about 45 degrees Celsius, or about 38 to about 43 degrees Celsius (about 100 to about 110 degrees Fahrenheit).

In some embodiments, the first cooling apparatus is a heat exchanger. In some embodiments, the second liquid stream is heated with the first vapor stream. In some embodiments, the first liquid stream is substantially free of light hydrocarbons.

EXAMPLES

The Examples that follow are illustrative of specific embodiments of the methods and apparatuses disclosed herein, and various uses thereof. They are set forth for explanatory purposes only, and are not to be taken as limiting the disclosure.

Example 1: Transalkylation Process with Benzene Recovery—Single Separator

As shown in FIG. 1, a feed stream 102 including C9+ aromatics and toluene is heated in a feed/effluent heat exchanger 104 and further heated in a transalkylation furnace 108 and then fed to a transalkylation (TA) reactor 112. Stream 102 includes both the fresh toluene and C9+ aromatics fed to the process as well as all toluene and C9+ recycle. The effluent 114 from reactor 112 is cooled in the TA feed effluent heat exchanger 104, a TA stabilizer feed preheater 118, and a TA effluent cooler 122 and enters a low-temperature flash drum 126 where it is separated into a vapor stream 128 and a liquid stream 142. Thus, the TA reactor effluent 114 is used both to heat the feed stream 102 in the feed effluent heat exchanger 104, and also to preheat the liquid stream from the flash drum 142 in the TA stabilizer feed preheater 118.

The vapor stream 128 from the flash drum 126 is split, with a portion 130 of the stream vented as fuel gas, and the other portion 132 combined with a hydrogen make-up stream 134, then compressed in a TA recycle gas compressor 138 into a recycle stream 140, which is recycled to the TA reactor feed stream 102.

The liquid stream 142 from the flash drum 126 is heated in the stabilizer feed preheater 118 to form a stabilizer feed stream 144, which is then provided to a stabilizer column 146, which separates the stabilizer feed stream 144 into a stabilizer column top stream 148 including light hydrocarbons, and a stabilizer column bottom stream 166 including benzene and C7+ hydrocarbons, including toluene, xylenes, and heavy aromatics.

The stabilizer column top stream 148 is condensed in a stabilizer condenser 150 to form a two-phase mixture 152, which is separated in a stabilizer reflux drum 154 into a vapor stabilizer vent stream 156 and a liquid stream 158. The liquid stream 158 passes through a stabilizer reflux pump 160, after which it is split into a light hydrocarbon product stream 162 and a reflux stream 164, the latter of which is sent back to the stabilizer column 146.

The stabilizer column bottoms stream 166 is sent through a stabilizer bottoms pump 168, then split into two streams 170 and 176. The first stream 170 is sent through a stabilizer reboiler 172, and the resulting reboiled stream 174 is sent back to the stabilizer column 146. The second stream 176 is a benzene column feed stream that is sent to a benzene column 178.

The feeds to benzene column 178 include stream 176 and stream 177. Stream 177 is combined with stream 176 prior to being fed into the benzene column 178. In the aromatics complex, benzene is recovered from both the disproportionation or transalkylation units and the extractive distillation and purified. Rather than build duplicate benzene columns to do this, most aromatics complexes use a single benzene column that is shared. Stream 177 is extract from the extractive distillation unit in the aromatics complex. The benzene column 178 separates the benzene column feed stream 176 and stream 177 into a benzene column top stream 180 including benzene and a benzene column bottom stream 194 including C7+ hydrocarbons, including toluene, xylenes, and heavy aromatics. The benzene column top stream 180 is condensed in a benzene tower condenser 182 to form a stream 184, which is sent through a benzene tower reflux drum 186 and a benzene tower reflux pump 188, then split into a benzene drag stream 189 and a benzene reflux stream 192, which is returned to the benzene column 178. The benzene column has a sidedraw stream 190 located above the feed where the benzene steam is produced. The benzene drag stream 189 typically has zero flowrate. However, if substances with boiling points less than that of benzene are present in the benzene column, the benzene drag stream can be used to collect the impurities, route them appropriately, for example recycle them to the extractive distillation unit, and continue to produce benzene that meets purity specifications.

The benzene column bottom stream 194 is sent through a benzene tower bottoms pump 195, then split into two streams 196 and 199. The first stream 196 is sent through a benzene tower reboiler 197, and the resulting reboiled stream 198 is sent back to the benzene column 178. The second stream 199 is a C7+ product stream that includes toluene, xylenes, and heavy aromatics. Stream 199 is typically sent to the transalkylation unit toluene column (not shown for this example).

To illustrate the improved energy efficiency of the disclosure, a computer model was made using Aspen Plus to simulate the process shown in FIG. 1. The transalkylation reactor conditions shown above were used to simulate reactor operations. At these conditions, toluene per-pass conversion was 31.1% and C9 aromatic per-pass conversion was 47.6%. Reactor yields were similar to typical yields observed during operations. Typical operating parameters were used in the computer simulation for the other equipment shown in FIG. 1. The flow rate of stream 189 was 0.0 kg/h.

The results obtained are shown in Table 1. In this case, an approach temperature of 28° C. (50° F.) was used in exchanger 104. The duty for furnace 108 shown in Table 1 was relatively modest and much smaller than the duties for reboilers 172 and 197. This illustrates that most of the energy consumed in the transalkylation process is for distillation.

TABLE 1

Results from Aspen Plus Simulation for Process in FIG. 1

| | Duty, MMkcal/h (watts) | | | Temp., °C | Mass Flowrate, metric ton/h (kg/s) | | | | | | | |
|---|---|---|---|---|---|---|---|---|---|---|---|---|
| Element Number | 108 (furnace) | 172 (stabilizer reboiler) | 197 (benzene tower reboiler) | 116 | 130 | 134 | 177 | 156 | 162 | 189 | 190 | 199 |
| | 7.5 $(8.7 \times 10^6)$ | 21.3 $(2.5 \times 10^7)$ | 55.7 $(6.5 \times 10^7)$ | 123 | 8.2 (2.3) | 2.9 (0.8) | 114.3 (31.8) | 6.2 (1.7) | 3.0 (0.8) | 0.0 (0.0) | 66.4 (18.4) | 342.2 (95.1) |

Example 2A: Transalkylation Process with Benzene Recovery—Dual Separator

Figure 2:
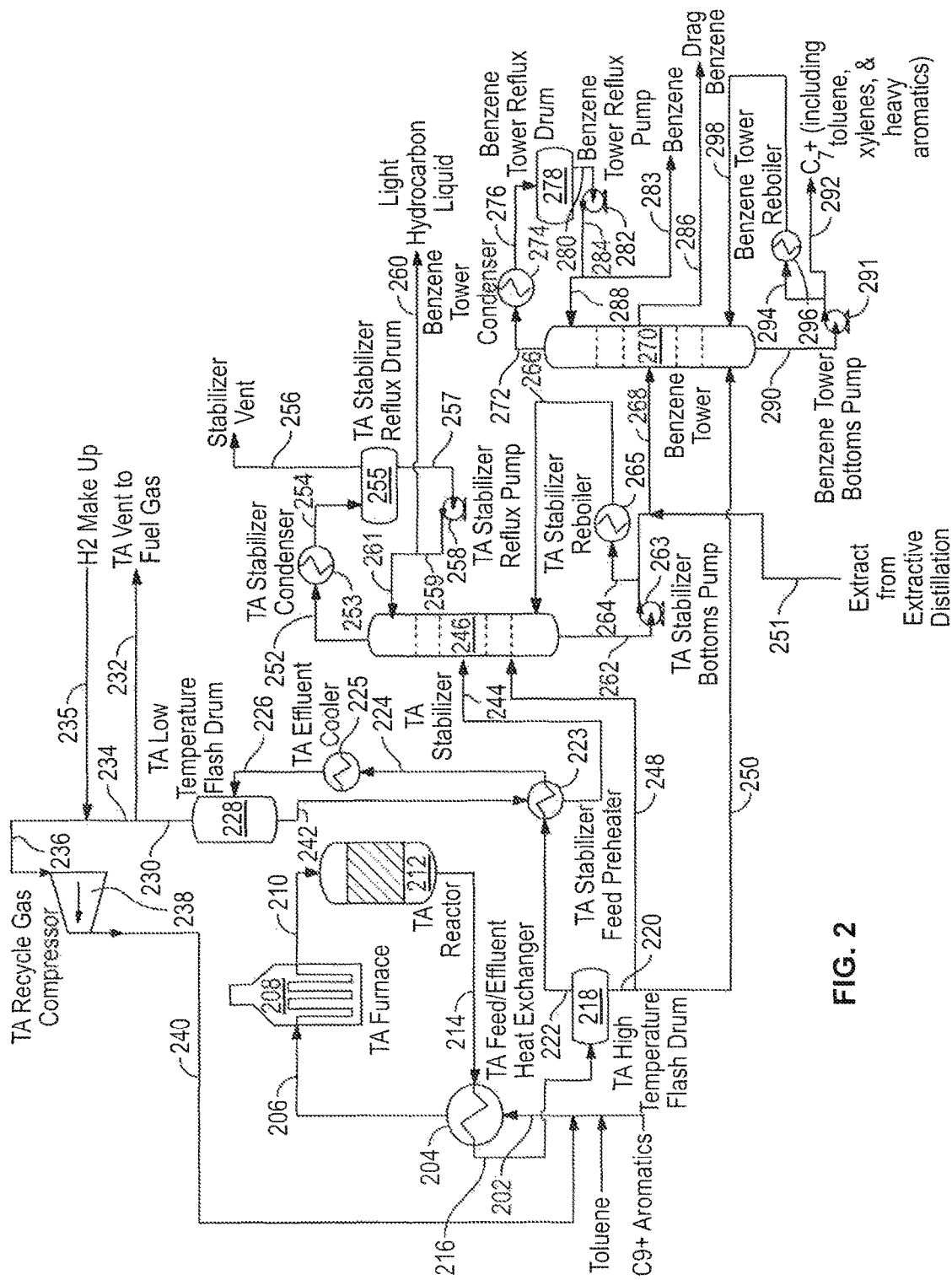
FIG. 2 is a schematic representation of a transalkylation process with benzene recovery, wherein a portion of a liquid stream bypasses a stabilizer column and is sent to a benzene column.

As shown in FIG. 2, a feed stream 202 including C9+ aromatics and toluene is heated in a transalkylation furnace 208 and then fed to a transalkylation (TA) reactor 212. Stream 202 includes both the fresh toluene and C9+ aromatics fed to the process as well as all toluene and C9+ recycle. The TA reactor effluent 214 then is used to heat the feed stream 202 in a feed/effluent heat exchanger 204, which produces a high-temperature two-phase mixture 216. The high-temperature two-phase mixture 216 is sent to a high-temperature flash drum 218, where it is separated into a high-temperature liquid stream 220 and a high-temperature vapor stream 222.

The vapor stream 222 from the high-temperature flash drum 218 is used to preheat the liquid stream 242 from a low-temperature flash drum 228 in a TA stabilizer feed preheater 223. The vapor stream 224 is then further cooled in a TA effluent cooler 225 to produce a low-temperature two-phase mixture 226. The low-temperature two-phase mixture 226 is sent to the low-temperature flash drum 228, which separates the low-temperature two-phase mixture 226 into a low-temperature vapor stream 230 and a low-temperature liquid stream 242.

The low-temperature vapor stream 230 is split, with a portion of the stream 232 vented as fuel gas, and the other portion 234 combined with a hydrogen make-up stream 235 to form stream 236, then compressed in a recycle gas compressor 238 to produce recycle stream 240. The recycle stream 240 is recycled to the TA reactor feed stream 202.

The low-temperature liquid stream 242 from the low-temperature flash drum 228 is preheated with the vapor stream 222 from the high-temperature flash drum 218 in a stabilizer feed preheater 223 to form a stabilizer feed stream 244, which is then provided to a stabilizer column 246. Also provided to the stabilizer column is optionally a portion 248 of the high-temperature liquid stream 220 from the high-temperature flash drum 218.

The stabilizer column 246 separates the incoming streams into a stabilizer column top stream 252 including light hydrocarbons, and a stabilizer column bottom stream 262 including benzene and C7+ hydrocarbons, including toluene, xylenes, and heavy aromatics.

The stabilizer column top stream 252 is condensed in a stabilizer condenser 253 and the resulting two-phase mixture 254 is separated in a stabilizer reflux drum 255 and vapor stream 256 is vented. A liquid stream 257 from the drum is sent through a stabilizer reflux pump 258 and then split into a light hydrocarbon product stream 260 and a reflux stream 261, the latter of which is sent back to the stabilizer column 246.

The stabilizer column bottom stream 262 is sent through a stabilizer bottoms pump 263, then split into a benzene column feed stream 268 and a stream 264 that is reboiled in a stabilizer reboiler 265. The reboiled stream 266 is sent back to the stabilizer column. The benzene column feed stream 268 is sent to a benzene column 270.

At least a portion 250 of the high-temperature liquid stream 220 from the high-temperature flash drum 218 is provided directly to the benzene column 270, and bypasses the stabilizer column 246.

The benzene column 270 separates the benzene column feed streams 250, 251, and 268 into a benzene column top stream 272 including benzene and a benzene column bottom stream 290 including C7+ hydrocarbons, including toluene, xylenes, and heavy aromatics. Stream 251 is combined with stream 268 prior to being fed into the benzene column 270. Stream 251 is extract from the extractive distillation unit. The benzene column top stream 272 is condensed in a benzene tower condenser 274 to form stream 276, which is sent to a benzene tower reflux drum 278 and a benzene tower reflux pump 282, then split into a benzene drag stream 283 and a reflux stream 288 that is sent back to the benzene column 270. The benzene column has a sidedraw stream 286 located above the feed where the benzene steam is produced.

The benzene column bottoms stream 290 sent to a benzene tower bottoms pump 291 and is split into a reboiled stream 298 that is sent back to the benzene column 270 and a C7+ product stream 292 including toluene, xylenes, and heavy aromatics.

The Aspen Plus model described above was modified to simulate the process shown in FIG. 2. For this example, all the conditions were kept the same as Example 1 and all of stream 220 was sent to the stabilizer via stream 248 (i.e. stream 250=0.0 kg/h). Table 2 shows the results of this simulation. Since the reactor was operated the same as in Example 1, the reactor product was the same, and it was expected that directing material to the stabilizer would also yield the same duty in the stabilizer reboiler. It was surprising when the results showed that the duty was nearly 7% lower. In an aromatics complex with an inefficient selective adsorption based paraxylene plant, the energy for the stabilizer reboiler is supplied by the surplus waste heat from the selective adsorption plant, so saving energy in the stabilizer reboiler may not be very important. However when a low energy crystallization based paraxylene plant is used in the aromatics complex, the energy savings shown in Table 2A are significant.

TABLE 2A

Results from Aspen Plus Simulation for Process in FIG. 2 at Exchanger Approach Temperature = 28° C.

| | Duty, MMkcal/h (watts) | | | Temp., ° C. | | | Mass Flowrate, metric ton/h (kg/s) | | | | | | |
|---|---|---|---|---|---|---|---|---|---|---|---|---|---|
| Element Number | 208 (furnace) | 265 (stabilizer reboiler) | 296 (benzene tower reboiler) | 216 | 232 | 235 | 251 | 256 | 260 | 283 | 286 | 292 | |
| | 7.6 ($8.8 \times 10^6$) | 19.8 ($2.3 \times 10^7$) | 55.7 ($6.5 \times 10^7$) | 123 | 10.3 (2.9) | 3.3 (0.9) | 114.3 (31.8) | 4.8 (1.3) | 2.7 (0.8) | 0.0 (0.0) | 66.2 (18.4) | 342.2 (95.1) | |

Example 2B: Transalkylation Process with Benzene Recovery—Dual Separator

This example illustrates adjustment of the transalkylation process conditions was used to lower the stabilizer reboiler duty even more.

Table 2A showed that the TA vent is a little larger and the H2 make up is a little larger than Example 1. This is apparently because using the high temperature flash drum 218 changes the composition of the material in the low temperature flash drum resulting in a little more benzene in stream 230. The simulations for Examples 1 and 2A kept the 112 content of recycle gas stream 240 the same at 80 mol %. When the benzene content in stream 218 increased in Example 2A, the resulted in a larger vent. The larger vent also increased 112 loss and the H2 make up increased.

In this example, the parameters used in the Aspen Plus simulation were the same as Example 2A except the approach temperature in heat exchanger 204 was increased to 33° C. (60° F.). Table 2B shows that the stabilizer reboiler duty in this example is about 9% lower than the stabilizer duty from Example 1, which results in even more energy savings. Table 2B shows that there are additional savings from operating the process at these conditions because the 112 make up has decreased significantly and the vent has dropped to zero. Hydrogen is an expensive raw material for the transalkylation process so these savings are very important. It is important to note that decreasing the approach temperature in exchanger 204 has increased the duty of furnace 208 modestly. Depending on the sources of fuel and energy in the aromatics complex, this modest increase may not be significant. It may be economically advantageous to operate in this mode as compared with the mode illustrated in Example 2A.

Example 2C: Transalkylation Process with Benzene Recovery—Dual Separator

This example illustrates that even more energy savings were achieved when material from the high temperature flash drum is sent to the benzene tower using stream 250. The Aspen Plus model was run at the same conditions as Examples 1 and 20% of the material from stream 220 was fed to the benzene tower via stream 250. The results are shown in Table 2C. It was very surprising that diverting 20% of stream 220 to the benzene column lowered the duty of the stabilizer by 20% while only increasing the duty of the benzene tower reboiler 296 by only 1%. These results showed that it was possible to significantly decrease the energy used in the transalkylation unit when a portion of the liquid from the high temperature flash drum bypasses the stabilizer column and is sent to the benzene column. The flowrate of the drag stream was only 876 kg/h in this case. This stream is recycled back to the extractive distillation unit. Even more energy savings were possible when more than 20% of the high temperature liquid bypassed the stabilizer column. The amount of energy savings is only limited by the increase in the duty in reboiler 296 and the flowrate of stream 189.

TABLE 2B

Results from Aspen Plus Simulation for Process in FIG. 2 at Exchanger Approach Temperature = 33° C.

| | Duty, MMkcal/h (watts) | | | Temp., ° C. | | | Mass Flowrate, metric ton/h (kg/s) | | | | | | |
|---|---|---|---|---|---|---|---|---|---|---|---|---|---|
| Element Number | 208 (furnace) | 265 (stabilizer reboiler) | 296 (benzene tower reboiler) | 216 | 232 | 235 | 251 | 256 | 260 | 283 | 286 | 292 | |
| | 10.3 ($1.2 \times 10^7$) | 19.3 ($2.2 \times 10^7$) | 55.7 ($6.5 \times 10^7$) | 129 | 0.0 (0.0) | 3.3 (0.9) | 114.3 (31.8) | 4.8 (1.3) | 2.7 (0.8) | 0.0 (0.0) | 66.2 (18.4) | 342.2 (95.1) | |

TABLE 2C

Results from the Aspen Plus Simulation for the Process in FIG. 2 Stream 250 = 20% of Stream 220.

| | Duty, MMkcal/h (watts) | | | Temp., ° C. | | | Mass Flowrate, metric ton/h (kg/s) | | | | | | |
|---|---|---|---|---|---|---|---|---|---|---|---|---|---|
| Element Number | 208 (furnace) | 265 (stabilizer reboiler) | 296 (benzene tower reboiler) | 216 | 232 | 235 | 251 | 256 | 260 | 283 | 286 | 292 |
| | 7.6 (8.8 × 10$^6$) | 17.0 (2.0 × 10$^7$) | 56.4 (6.6 × 10$^7$) | 123 | 10.3 (2.9) | 3.3 (0.9) | 114.3 (31.8) | 4.8 (1.3) | 2.7 (0.8) | 0.0 (0.0) | 66.2 (18.4) | 342.2 (95.1) |

Figure 3:
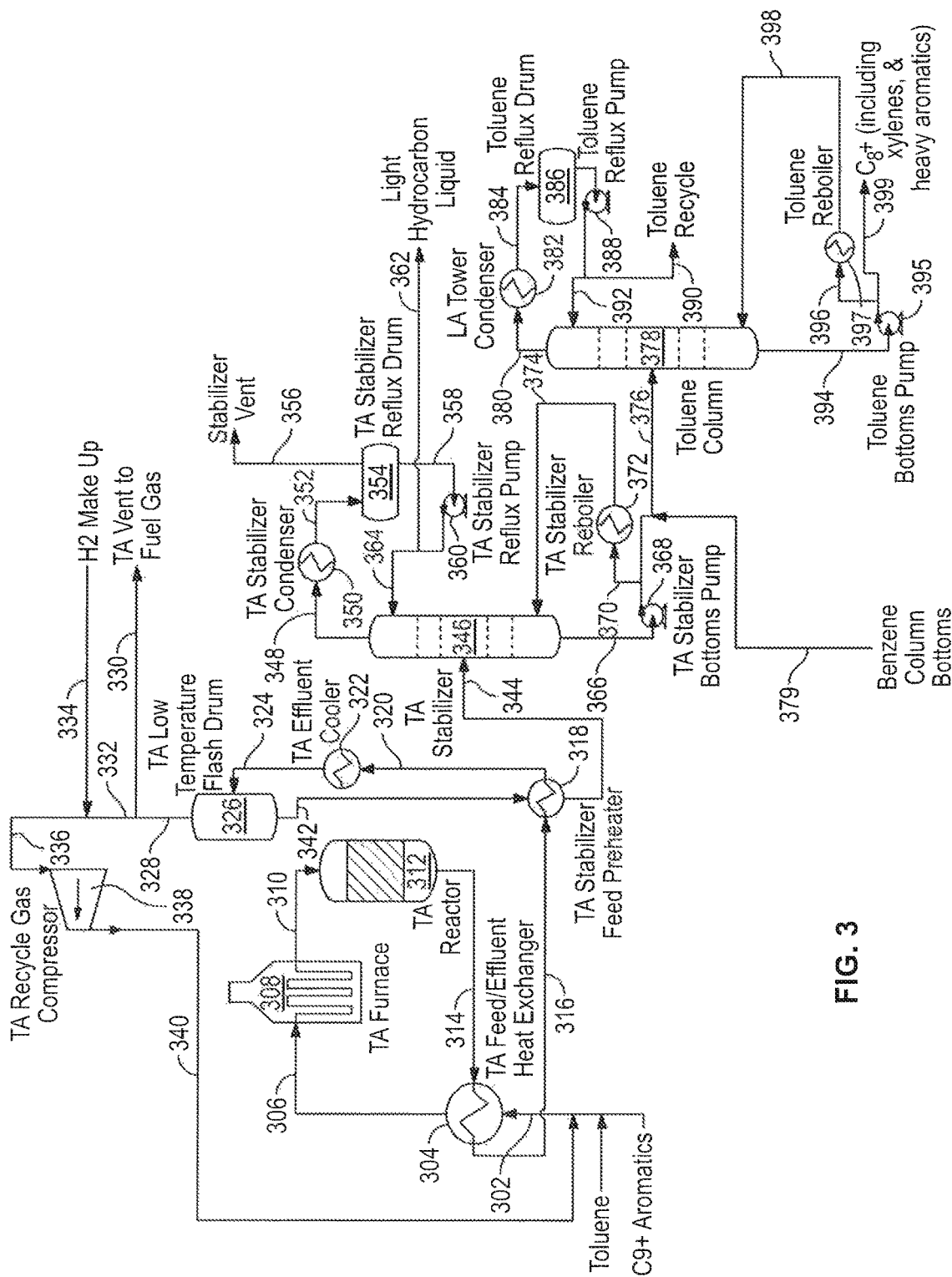
FIG. 3 is a schematic representation of a transalkylation process where the stabilizer column bottoms is sent to a toluene column.

Example 3: Transalkylation Process with Light Aromatics Recovery—Single Separator FIG. 3 shows a transalkylation process in a case where benzene cannot be produced directly by distillation. Whether benzene can be produced directly by distillation or not depends mostly on the performance of the transalkylation catalyst and properties of the feed to the transalkylation unit. When benzene cannot be produced directly by distillation, the benzene is typically recovered in the light hydrocarbon liquid stream leaving the stabilizer, and the stabilizer bottoms is sent to a toluene column.

A feed stream 302 including C9+ aromatics and toluene is heated in a feed/effluent heat exchanger 304 and further heated in a transalkylation furnace 308 and then fed to a transalkylation (TA) reactor 312. Stream 302 includes both the fresh toluene and C9+ aromatics fed to the process as well as all toluene and C9+ recycle. The effluent 314 is then cooled in the TA feed effluent heat exchanger 304, a TA stabilizer feed preheater 318, and a TA effluent cooler 322, and then enters a low-temperature flash drum 326 where it is separated into a vapor stream 328 and a liquid stream 342. Thus, the TA reactor effluent 314 is used both to heat the feed stream 302 in the feed effluent heat exchanger 304, and also to preheat the liquid stream from the flash drum 342 in the TA stabilizer feed preheater 318.

The vapor stream 328 from the flash drum 326 is split, with a portion 330 of the stream vented as fuel gas, and the other portion 332 combined with a hydrogen make-up stream 334, then compressed in a TA recycle gas compressor 338 into a recycle stream 340, which is recycled to the TA reactor feed stream 302.

The liquid stream 342 from the flash drum 326 is heated in the stabilizer feed preheater 318 and then provided to a stabilizer column 346, which separates the stabilizer feed stream 344 into a stabilizer column top stream 348 including light hydrocarbons and benzene, and a stabilizer column bottom stream 366 including benzene and C7+ hydrocarbons, including toluene, xylenes, and heavy aromatics.

The stabilizer column top stream 348 is condensed in a stabilizer condenser 350 to form a two-phase mixture 352, which is separated in a stabilizer reflux drum 354 into a vapor stabilizer vent stream 356 and a liquid stream 358. The liquid stream 358 passes through a stabilizer reflux pump 360, after which it is split into a light hydrocarbon product stream 362 and a reflux stream 364, the latter of which is sent back to the stabilizer column 346. Most of the benzene in the feed to the stabilizer is recovered in the light hydrocarbon liquid and is recycled to the extractive distillation unit.

The stabilizer column bottoms stream 366 is sent through a stabilizer bottoms pump 368, then split into two streams 370 and 376. The first stream 370 is sent through a stabilizer reboiler 372, and the resulting reboiled stream 374 is sent back to the stabilizer column 346. The second stream 376 is a toluene column feed stream that is sent to a toluene column 378. Stream 376 comprises nearly all of the toluene and only a small portion of the benzene fed to the stabilizer. In an aromatics complex, the bottoms stream from the extractive distillation unit benzene column (not shown) is fed to toluene column 378 in the transalkylation unit. This benzene column bottoms stream is stream 379.

The toluene column 378 boils toluene to produce a toluene column top stream 380 including toluene and a toluene column bottom stream 394 including C8+ hydrocarbons, including xylenes and heavy aromatics. The toluene column top stream 380 is condensed in a toluene column condenser 382 to form a stream 384, which is sent through a toluene column reflux drum 386 and a toluene column reflux pump 388, then split into a toluene stream 390 including benzene, toluene, and co-boiling non-aromatics that is recycled to the transalkylation unit feed, and a toluene reflux stream 392, which is returned to the toluene column 378.

The toluene column bottom stream 394 is sent through a toluene column bottoms pump 395, then split into two streams 396 and 399. The first stream 396 is sent through a toluene column reboiler 397, and the resulting reboiled stream 398 is sent back to the toluene column 378. The second stream 399 is a C8+ product stream that includes xylenes and heavy aromatics. In an aromatics complex, this stream is sent to the paraxylene unit.

The Aspen Plus model described above was modified to simulate the process shown in FIG. 3. In this case, the model was adjusted to show what happens to the duty of the stabilizer reboiler 372 when the benzene in feed stream 344 is boiled overhead into streams 356 and 362. Table 3 shows that the stabilizer reboiler duty more than doubled when compared with the results in Table 1, where most of the benzene was recovered in the bottom of the stabilizer. This also resulted in a significant increase in the flowrate of the stabilizer light hydrocarbon overhead liquid stream, as expected since the purpose of this design is to push the benzene there and recycle it back to extractive distillation. These results show that significantly more energy is needed in the transalkylation unit when benzene cannot be produced directly by distillation.

TABLE 3

Results from Aspen Plus Simulation for Process in FIG. 3

| | Duty, MMkcal/h (watts) | | | Temp., °C | Mass Flowrate, metric ton/h (kg/s) | | | | | |
|---|---|---|---|---|---|---|---|---|---|---|
| Element Number | 308 (furnace) | 372 (stabilizer reboiler) | 397 (toluene reboiler) | 316 | 330 | 334 | 356 | 362 | 390 | 399 |
| | 8.1 ($9.4 \times 10^6$) | 43.3 ($5.0 \times 10^7$) | 26.1 ($3.0 \times 10^7$) | 125 | 8.2 (2.3) | 3.0 (0.8) | 2.4 (0.7) | 51.1 (14.2) | 159.5 (44.3) | 103.1 (28.6) |

Example 4A: Transalkylation Process with Benzene Recovery—Dual Separator

One way to reduce the energy consumed in stabilizer reboiler when benzene is not produced by distillation would be to use a high temperature flash drum to separate the effluent from the feed/effluent heat exchanger into a high-temperature liquid stream and a high-temperature vapor stream and bypass at least a portion of the high-temperature liquid stream to the stabilizer or benzene column. This is another embodiment of the invention illustrated in Examples 2A, 2B, and 2C.

Example 4B: Transalkylation Process with Benzene Recovery—Dual Separator

Another way to reduce the energy consumed in stabilizer reboiler when benzene is not produced by distillation would be to use a high temperature flash drum to separate the effluent from the feed/effluent heat exchanger into a high-temperature liquid stream and a high-temperature vapor stream and bypass at least a portion of the high-temperature liquid stream to the toluene column, such as toluene column 378 in FIG. 3. The Aspen Plus model was used to evaluate this example. The liquid stream from the high temperature flash drum contained benzene and other low boiling point hydrocarbons. In the example shown in FIG. 2, these hydrocarbons ended up in the benzene drag stream. The toluene column does not typically have a drag stream connection where these hydrocarbons can be recovered and routed correctly. Consequently, when a portion of the liquid stream from the high temperature flash drum was directed to the toluene column, the light hydrocarbons and benzene were sent with the toluene recycle back to the transalkylation reactor. The Aspen Plus model showed that they built up to unacceptable levels in this recycle loop. Furthermore, some of the recycled benzene was converted to low value light hydrocarbons in the transalkylation reactor. These Aspen Plus results showed that when benzene is not produced by distillation, using a high temperature flash drum to separate the effluent from the feed/effluent heat exchanger bypassing at least a portion of the high-temperature liquid stream to the toluene column did not improve the energy consumption and process economics of the transalkylation process.

Example 4C: Transalkylation Process with Benzene Recovery—Dual Separator

Figure 4:
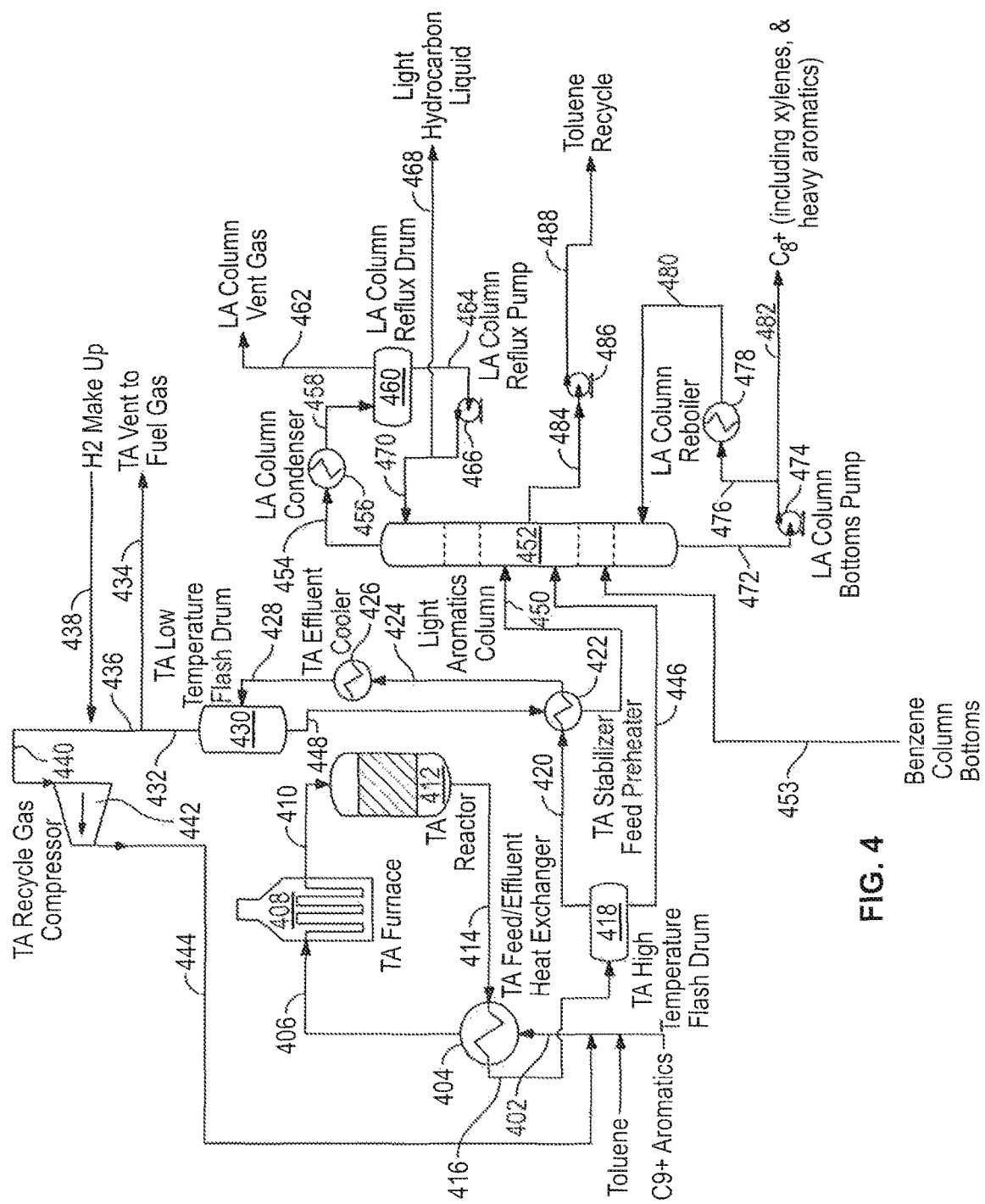
FIG. 4 is a schematic representation of a transalkylation process with light aromatic recovery with only one distillation column.

FIG. 4 shows a transalkylation process in a case where benzene cannot be produced directly by distillation, and which offers energy savings compared to the process shown in FIG. 3.

A feed stream 402 including C9+ aromatics and toluene is heated in a feed/effluent heat exchanger 404 and further heated in a transalkylation furnace 408 and then fed to a transalkylation (TA) reactor 412. Stream 402 includes both the fresh toluene and C9+ aromatics fed to the process as well as all toluene and C9+ recycle. The TA reactor effluent 414 then is used to heat the feed stream 402 in the feed/effluent heat exchanger 404, which produces a high-temperature two-phase mixture 416. The high-temperature two-phase mixture 416 is sent to a high-temperature flash drum 418, where it is separated into a high-temperature liquid stream 446 and a high-temperature vapor stream 420.

The vapor stream 420 from the high-temperature flash drum 418 is used to preheat the liquid stream 448 from a low-temperature flash drum 430 in a stabilizer feed pre-heater 422, and then is further cooled in an effluent cooler 426 to produce a low-temperature two-phase mixture 428. The low-temperature two-phase mixture 428 is sent to the low-temperature flash drum 430, which separates the low-temperature two-phase mixture 428 into a low-temperature vapor stream 432 and a low-temperature liquid stream 448. The low-temperature vapor stream 432 is split, with a portion 434 of the stream vented as fuel gas, and the other portion 436 combined with a hydrogen make-up stream 438, then compressed in a recycle gas compressor 442 to produce a recycle stream 444, which is recycled to the TA reactor feed stream 402.

The low-temperature liquid stream 448 from the low-temperature flash drum 430 is preheated with the vapor stream 420 from the high-temperature flash drum 418, then the resulting light aromatics column feed stream 450 is provided to a light aromatics column 452. Also provided to the light aromatics column 452 is the high-temperature liquid stream 446 from the high-temperature flash drum 418. In an aromatics complex, the bottom stream from the extractive distillation unit benzene column (not shown) is may also be provided to the light aromatics column 452. This benzene column bottoms stream is stream 453.

The light aromatics column 452 co-boils benzene and toluene and separates the incoming streams into a light aromatics column top stream 454 including light hydrocarbons and benzene, a light aromatics column bottom stream 472 including C8+ hydrocarbons, including xylenes and heavy aromatics, and a light aromatics column side stream 484 including toluene. The light aromatics column side stream 484 is recycled within the transalkylation unit.

The light aromatics column top stream 454 is condensed in a light aromatics condenser 456 to produce a two-phase mixture 458, which is separated in a light aromatics reflux drum 460 into a light aromatics vent gas stream 462 and a liquid stream 464. The liquid stream 464 from the drum 460 is split into a light hydrocarbon product stream 468 and a reflux stream 470, the latter of which is sent back to the light aromatics column 452.

The light aromatics column bottom stream 472 is sent through a light aromatics bottoms pump 474, then split into two streams 482 and 476. Stream 482 is a C8+ product stream including xylenes and heavy aromatics. Stream 476 is reboiled in a light aromatics reboiler 478 to produce a reboiled stream 480. In an aromatics complex, stream 472 is sent to the paraxylene unit. Reboiled stream 480 is sent back to the light aromatics column 452.

The process depicted in FIG. 4 provides energy savings over the process depicted in FIG. 3 because the FIG. 4 process requires only a single distillation column 452, whereas the FIG. 3 process uses two distillation columns—a stabilizer column 346 and a light aromatics column 378.

Having described the methods and apparatuses disclosed herein in detail and by reference to specific embodiments thereof, it will be apparent that modifications and variations are possible without departing from the scope of the disclosure as set forth in the appended claims. More specifically, although some aspects of the present disclosure are identified herein as particularly advantageous, it is contemplated that the present methods and apparatuses are not necessarily limited to these particular aspects.

The invention claimed is:

1. A process comprising the steps of:
   (a) reacting, in a reactor, a reactor feed stream comprising toluene, C9 aromatics, C10 aromatics, and hydrogen over a catalyst to produce a reactor effluent stream comprising benzene and xylenes;
   (b) cooling the reactor effluent stream to form a first two-phase mixture;
   (c) separating the first two-phase mixture into a first liquid stream and a first vapor stream;
   (d) providing at least a portion of the first liquid stream to a benzene column, wherein the portion of the first liquid stream provided to the benzene column does not contact a stabilizer column before being provided to the benzene column;
   (e) recovering benzene from the first condensed liquid stream in the benzene column;
   (f) cooling the first vapor stream to form a second two-phase mixture;
   (g) separating the second two-phase mixture into a second liquid stream and a second vapor stream; and
   (h) providing the second liquid stream to the stabilizer column.

2. The process of claim 1, wherein the first liquid stream is substantially free of light hydrocarbons.

3. The process of claim 1, further comprising using the reactor effluent stream to heat the reactor feed stream.

4. The process of claim 1, further comprising using the first vapor stream to heat the reactor feed stream.

5. The process of claim 1, wherein the reactor feed stream is heated to within about 50 degrees Celsius of the reactor effluent stream.

6. The process of claim 1, wherein the step of cooling the reactor effluent stream to form the first two-phase mixture is performed at between about ambient temperature and the reactor temperature.

7. The process of claim 1, wherein the step of cooling the first vapor stream to form the second two-phase mixture is performed at about ambient temperature.

8. The process of claim 1, further comprising using the first vapor stream to heat the second condensed liquid stream.

9. The process of claim 1, wherein the first liquid stream is not directed to a toluene column.

10. A process comprising the steps of:
    (a) reacting, in a reactor, a reactor feed stream comprising toluene, C9 aromatics, C10 aromatics, and hydrogen over a catalyst to produce a reactor effluent stream comprising benzene, toluene, and xylenes;
    (b) cooling the reactor effluent stream to form a first two-phase mixture;
    (c) separating the first two-phase mixture into a first liquid stream and a first vapor stream;
    (d) providing the first liquid stream to a stabilizer column to produce a side draw stream comprising benzene, toluene, and C8 aromatics;
    (e) providing the side draw stream to an extractive distillation unit;
    (f) cooling the first vapor stream to form a second two-phase mixture; and
    (g) separating the second two-phase mixture into a second liquid stream and a second vapor stream.

11. The process of claim 10, further comprising providing the second liquid stream to the stabilizer column.

12. The process of claim 10, wherein the first liquid stream is substantially free of light hydrocarbons.

13. The process of claim 10, further comprising using the reactor effluent stream to heat the reactor feed stream.

14. The process of claim 10, further comprising using the first vapor stream to heat the reactor feed stream.

15. The process of claim 10, wherein the reactor feed stream is heated to within about 50 degrees Celsius of the reactor effluent stream.

16. The process of claim 10, wherein the step of cooling the reactor effluent stream to form the first two-phase mixture is performed at between about ambient temperature and the reactor temperature.

17. The process of claim 10, wherein the step of cooling the first vapor stream to form the second two-phase mixture is performed at about ambient temperature.

18. The process of claim 10, further comprising using the first vapor stream to heat the second liquid stream.

* * * * *